(12) United States Patent
Melsheimer

(10) Patent No.: US 9,247,929 B2
(45) Date of Patent: Feb. 2, 2016

(54) DEFLECTABLE BIOPSY DEVICE

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/465,104

(22) Filed: May 7, 2012

(65) Prior Publication Data
US 2012/0220894 A1 Aug. 30, 2012

Related U.S. Application Data

(63) Continuation of application No. PCT/US2010/054420, filed on Oct. 28, 2010.

(60) Provisional application No. 61/261,857, filed on Nov. 17, 2009.

(51) Int. Cl.
*A61B 10/00* (2006.01)
*A61B 10/04* (2006.01)
A61B 10/02 (2006.01)
A61B 17/34 (2006.01)
A61B 1/00 (2006.01)
A61B 17/32 (2006.01)
A61B 17/00 (2006.01)
A61B 17/3205 (2006.01)
A61B 19/00 (2006.01)
A61B 17/29 (2006.01)

(52) U.S. Cl.
CPC ............ *A61B 10/04* (2013.01); *A61B 10/0275* (2013.01); *A61B 1/00133* (2013.01); *A61B 10/00* (2013.01); *A61B 10/02* (2013.01); *A61B 10/0233* (2013.01); *A61B 10/0266* (2013.01); *A61B 17/32002* (2013.01); *A61B 17/32053* (2013.01); *A61B 17/3421* (2013.01); *A61B 19/54* (2013.01); *A61B 2010/0093* (2013.01); *A61B 2010/0208* (2013.01); *A61B 2010/045* (2013.01); *A61B 2017/00331* (2013.01); *A61B 2017/00862* (2013.01); *A61B 2017/00867* (2013.01); *A61B 2017/2905* (2013.01); *A61B 2017/2927* (2013.01)

(58) Field of Classification Search
CPC ........................................................ A61B 5/00
USPC ........... 600/562, 564, 566, 567; 604/170, 164
See application file for complete search history.

(56) References Cited

U.S. PATENT DOCUMENTS

| | | | | |
|---|---|---|---|---|
| 3,342,175 A * | 9/1967 | Bulloch | ......................... | 600/567 |
| 4,684,369 A * | 8/1987 | Wildemeersch | .............. | 604/272 |
| 4,776,346 A * | 10/1988 | Beraha et al. | ................. | 600/567 |
| 4,817,631 A * | 4/1989 | Schnepp-Pesch et al. | .... | 600/566 |
| 4,966,162 A * | 10/1990 | Wang | ............................ | 600/563 |

(Continued)

FOREIGN PATENT DOCUMENTS

GB 2 403 419 A 1/2005
WO 2006/058195 A2 6/2006

*Primary Examiner* — Rene Towa
*Assistant Examiner* — May Abouelela
(74) *Attorney, Agent, or Firm* — Woodard, Emhardt, Moriarty, McNett & Henry LLP

(57) ABSTRACT

Disclosed is a deflectable biopsy device that includes a cannula having a preformed bend, wherein the shape of the cannula can be temporarily altered with the cannula returning to its original shape afterward. The deflectable biopsy device also includes a sampling member slidably disposed within the cannula and operable therewith to collect a tissue biopsy.

21 Claims, 10 Drawing Sheets

(56) References Cited

U.S. PATENT DOCUMENTS

| | | | |
|---|---|---|---|
| 4,986,279 A * | 1/1991 | O'Neill | 600/567 |
| 5,031,634 A | 7/1991 | Simon | |
| 5,152,749 A * | 10/1992 | Giesy et al. | 604/164.01 |
| 5,219,358 A | 6/1993 | Bendel et al. | |
| 5,242,448 A | 9/1993 | Pettine et al. | |
| 5,254,130 A * | 10/1993 | Poncet et al. | 606/206 |
| 5,285,795 A * | 2/1994 | Ryan et al. | 600/563 |
| 5,318,528 A * | 6/1994 | Heaven et al. | 604/95.01 |
| 5,334,185 A * | 8/1994 | Giesy et al. | 604/170.01 |
| 5,386,818 A | 2/1995 | Schneebaum et al. | |
| 5,469,853 A | 11/1995 | Law et al. | |
| 5,472,435 A * | 12/1995 | Sutton | 604/540 |
| 5,522,788 A | 6/1996 | Kuzmak | 600/141 |
| 5,545,141 A * | 8/1996 | Eld | 604/170.03 |
| 5,562,683 A | 10/1996 | Chan | |
| 5,601,572 A | 2/1997 | Middleman et al. | |
| 5,607,389 A | 3/1997 | Edwards et al. | |
| 5,807,304 A | 9/1998 | Cockburn | |
| 5,820,546 A | 10/1998 | Ouchi | |
| 5,830,220 A * | 11/1998 | Wan et al. | 606/139 |
| 5,833,692 A * | 11/1998 | Cesarini et al. | 606/79 |
| 5,904,692 A * | 5/1999 | Steckel et al. | 606/139 |
| 5,908,381 A | 6/1999 | Aznoian et al. | |
| 6,126,633 A * | 10/2000 | Kaji et al. | 604/95.04 |
| 6,419,641 B1 * | 7/2002 | Mark et al. | 600/564 |
| 6,572,593 B1 * | 6/2003 | Daum | 604/264 |
| 6,592,559 B1 * | 7/2003 | Pakter et al. | 604/272 |
| 6,875,219 B2 | 4/2005 | Arramon et al. | |
| 7,048,694 B2 * | 5/2006 | Mark et al. | 600/564 |
| 7,066,942 B2 | 6/2006 | Treace | |
| 7,282,020 B2 * | 10/2007 | Kaplan | 600/7 |
| 7,841,990 B2 * | 11/2010 | Mark et al. | 600/564 |
| 8,025,627 B2 * | 9/2011 | Freeman | 600/567 |
| 8,133,231 B2 * | 3/2012 | Martinek et al. | 606/88 |
| 8,172,744 B2 * | 5/2012 | Gellman et al. | 600/29 |
| 2004/0054377 A1 | 3/2004 | Foster et al. | |
| 2004/0133124 A1 * | 7/2004 | Bates et al. | 600/564 |
| 2004/0133168 A1 | 7/2004 | Salcudean et al. | |
| 2004/0162572 A1 | 8/2004 | Sauer | 606/170 |
| 2005/0004515 A1 * | 1/2005 | Hart et al. | 604/95.04 |
| 2005/0113714 A1 | 5/2005 | Mark et al. | 600/564 |
| 2006/0064062 A1 * | 3/2006 | Gurusamy et al. | 604/170.03 |
| 2006/0106324 A1 * | 5/2006 | Buckworth et al. | 600/567 |
| 2006/0129101 A1 * | 6/2006 | McGuckin | 604/164.01 |
| 2006/0167416 A1 * | 7/2006 | Mathis et al. | 604/164.01 |
| 2006/0189891 A1 * | 8/2006 | Waxman et al. | 600/564 |
| 2007/0197934 A1 * | 8/2007 | Vetter et al. | 600/564 |
| 2008/0243031 A1 * | 10/2008 | Seibel et al. | 600/566 |
| 2010/0185161 A1 * | 7/2010 | Pellegrino et al. | 604/272 |
| 2010/0298737 A1 * | 11/2010 | Koehler | 600/567 |
| 2012/0035501 A1 * | 2/2012 | Landrigan et al. | 600/567 |

* cited by examiner

DEFLECTABLE BIOPSY DEVICE

CROSS-REFERENCE TO RELATED APPLICATIONS

This application is a continuation of International Application No. PCT/US2010/054420, filed Oct. 28, 2010, which is hereby incorporated by reference. PCT/US2010/054420 claims the benefit of provisional Application No. 61/261,857 filed Nov. 17, 2009.

BACKGROUND

It is often desirable to perform a biopsy to sample selected tissue from a patient for medical evaluation. For example, biopsies can be useful in diagnosing various forms of cancer and other diseases affecting a localized area of tissue. However, access to some anatomical regions using present apparatus and methods can be difficult and/or dangerous due to obscure location(s) of the localized area. For example, a localized area could be obscured by obstacles such as bone, an artery or vein, ducts, nerves or organs. Such obstacles pose the possibility for unnecessary iatrogenic trauma during biopsy procedures.

Accordingly, there is a need for a biopsy apparatus and method that provide alternative modes of access to anatomical sites.

SUMMARY

Disclosed in one aspect is a deflectable biopsy device that includes a cannula having a preformed bend, wherein the shape of the cannula can be temporarily altered with the cannula returning to its original shape afterward. The deflectable biopsy device also includes a sampling member movably disposed within the cannula. The sampling member can include a wire slidably disposed within the cannula, the wire including a sampling cavity and a flexible portion, wherein the cannula and sampling member are slidable relative to one another between respective positions in which the sampling cavity is covered by or uncovered from the cannula.

This cannula can be inserted through an introducer laterally offset from the biopsy area with the preformed bend providing lateral displacement of the sampling cavity from the insertion site. This provides an alternate, indirect route to obtain the biopsy.

BRIEF DESCRIPTION OF THE DRAWINGS

FIG. 6b is a side elevational view of FIG. 6a.

DETAILED DESCRIPTION

Figure 1:
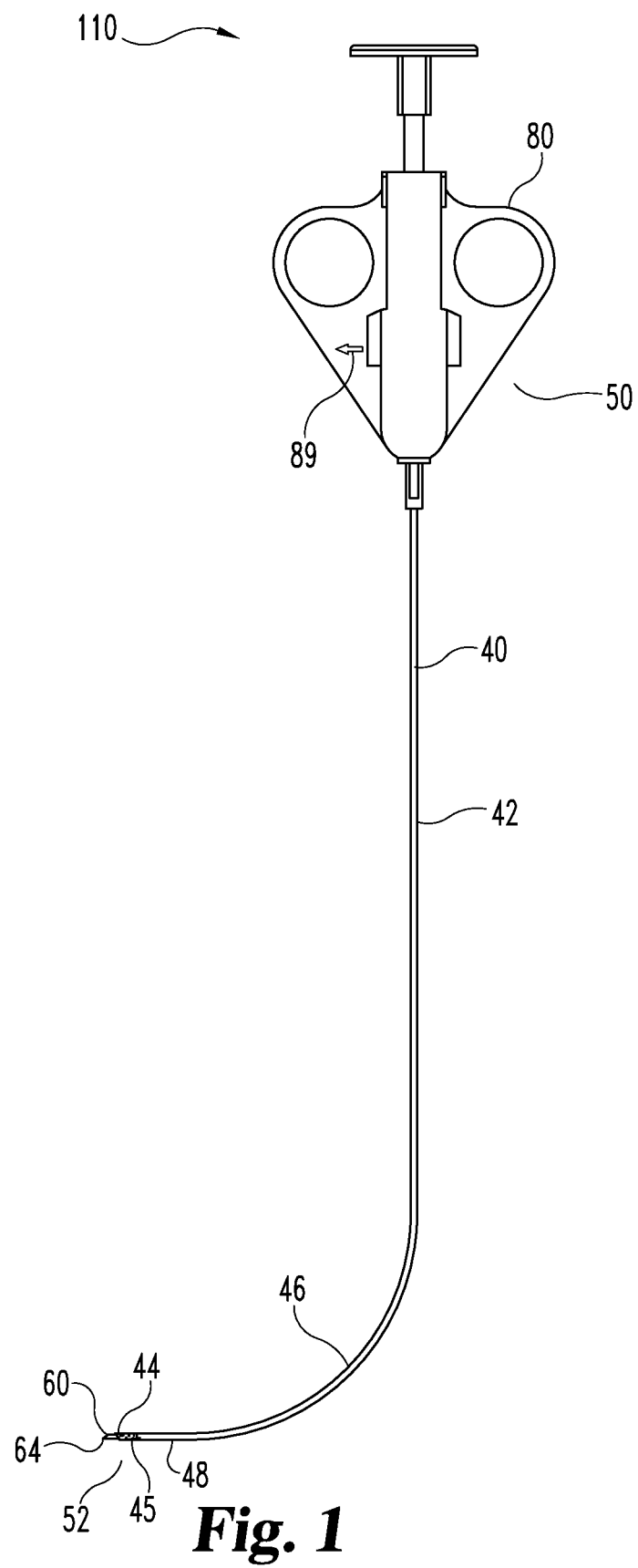
FIG. 1 is an elevational view of a deflectable biopsy device including a cannula, a wire and a firing mechanism.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

Referring to FIG. 1, one embodiment of a deflectable biopsy device 110 is illustrated including coring cannula 40, sampling member 60 and firing mechanism 80.

Figure 2:
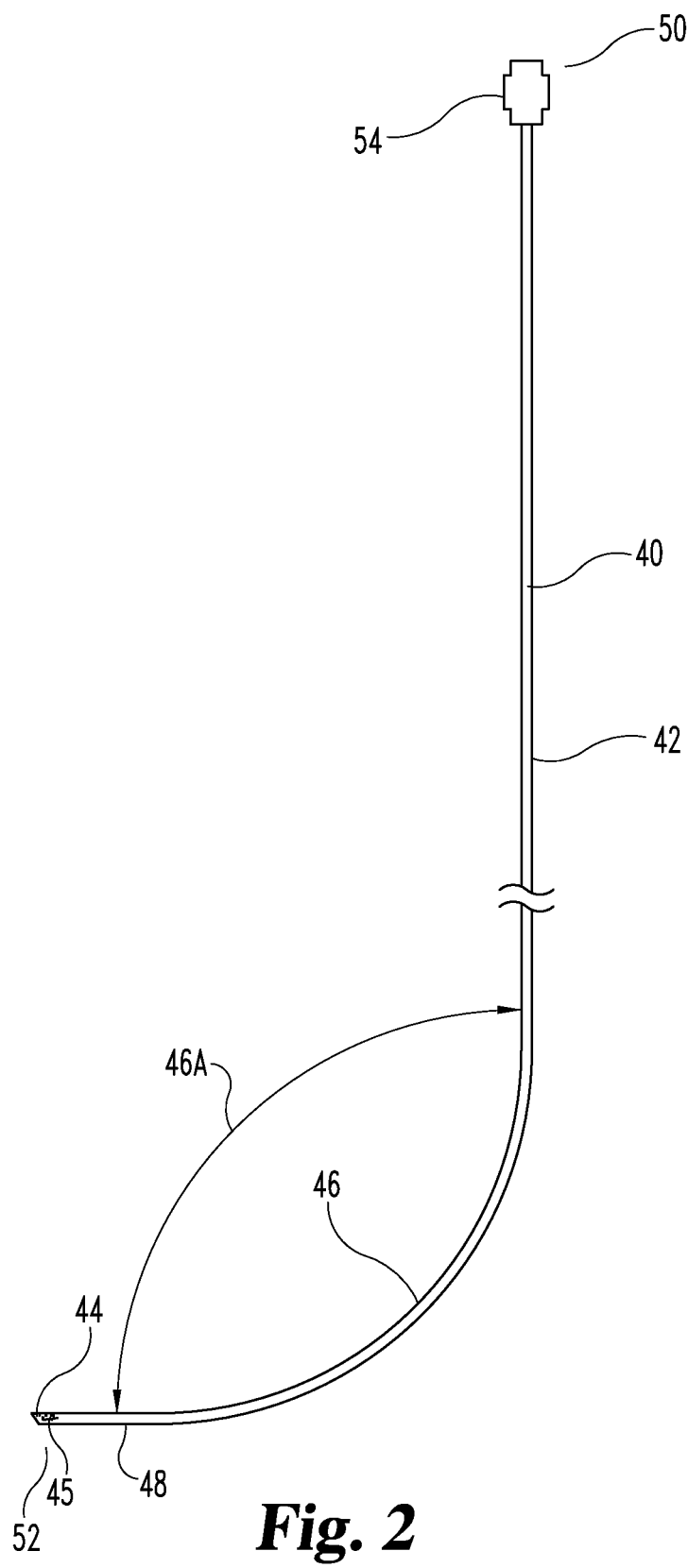
FIG. 2 is an elevational view of the cannula of FIG. 1.

Cannula 40, as illustrated in FIGS. 1 and 2, includes wall 42 defining a lumen between proximal end 50 and distal end 52 and including a preformed bend 46, straight walled portion 48 and tip 44. Cannula 40 may also optionally include visualization markers 45 as discussed below. In some embodiments, tip 44 is constructed and arranged to penetrate tissue, for example with a cutting edge. In the illustrated embodiment, tip 44 is pointed and bevel sharpened entirely around cannula 40 for cutting tissue. Needle cannula 40 can be soldered or otherwise affixed to hub 54 using one of selected well-known techniques, including that of Hall described in U.S. Pat. No. 5,354,623. Cannula 40 can be comprised of any suitable material, such as a plastic and/or metal material. In certain embodiments, cannula 40 comprises a superelastic alloy, for example, nitinol (Ni—Ti alloy), that permits elastic manipulation of cannula 40 beyond the point at which other metals would experience plastic deformation.

In embodiments where cannula 40 is formed of nitinol, preformed bend 46 can be imparted in the nitinol cannula 40 by deforming the cannula under heat for a prescribed period of time, which can produce a cannula entirely in the austenitic state, or by cold working the cannula. Cold working can convert a portion of crystalline structure of the bending zone of the cannula 40 into at least a partial martensitic condition while the unworked portions of the cannula, for example substantially straight portions proximal and/or distal of the bending zone, remain in the austenitic state. Cold worked Ni—Ti alloys are discussed in "Linear Superelasticity in Cold-Worked Ni—Ti", (Zadno and Duerig) pp. 414 to 419, in Engineering Aspects of Shape Memory Alloys, Butterworth-Heineman, Boston, Mass. (Duerig et al, editors). In addition to nitinol, superelastic or pseudoelastic copper alloys, such as Cu—Al—Ni, Cu—Al-Zi, and Cu-Zi are available as alternative cannula materials. Flexible polymeric materials with sufficient rigidity for both deployment and shape memory to assume a preformed bend may also be used in certain applications, either alone or in combination with reinforcing metal components, such as a metal braid or tip.

In the illustrated embodiment, preformed bend 46 curves cannula 40 approximately 90° relative to the longitudinal axis of cannula 40 proximate to proximal end 50. In alternative embodiments, preformed bend 46 can be configured to bend cannula 40 at least about 40°, typically about 40° to about 270°, and in certain embodiments between approximately 40° and approximately 90° relative to the longitudinal axis of cannula 40 proximate to proximal end 50. While the illustrative embodiment has a constant bend radius, other non-linear paths such as a variable bend radius can be used in other embodiments, for example, an increasing or decreasing bend radius. Furthermore, it is possible to introduce more than one preformed bend into cannula 40 for applications requiring a special configuration. The distal portion of cannula 40 can include straight walled portion 48 between distal end 52 and preformed bend 46. Straight walled portion 48 can be substantially straight or linear when in an unstressed condition.

Figure 3:
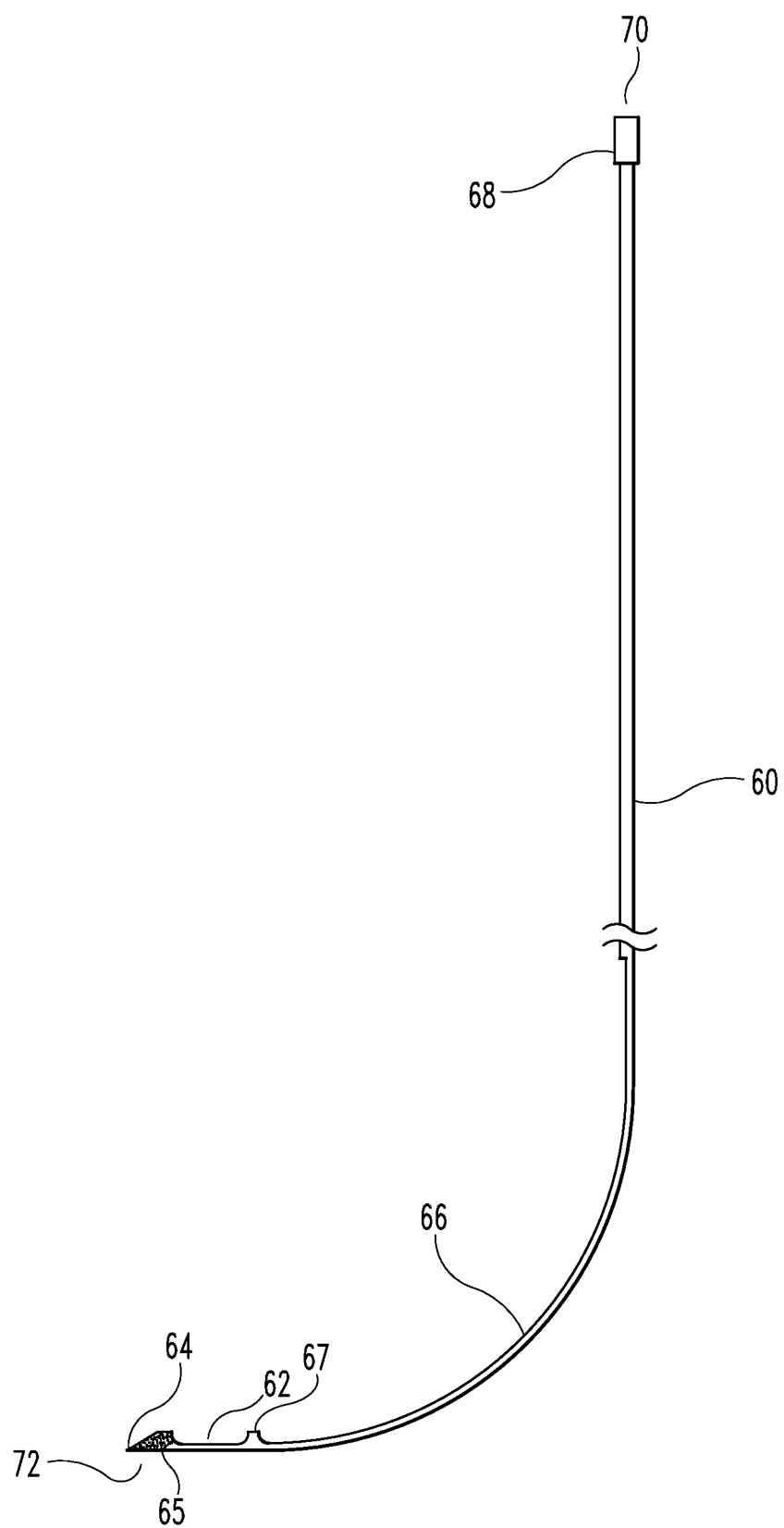
FIG. 3 is an elevational view of the wire of FIG. 1.

Sampling member 60, as illustrated in FIG. 3, includes sample cavity 62, tip 64 at distal end 72, shoulder 67, flexible portion 66 and hub 68 at proximal end 70. Sampling member 60 may also optionally include visualization markers 65 as discussed below. In one embodiment, sampling member 60 is constructed and arranged to transmit compressive, tensile and torsional forces between tip 64 and hub 68 with flexible portion 66 providing little resistance to bending so as to slidably navigate preformed bend 46 of cannula 40 without kinking or binding. Sampling member 60 can be comprised of any suitable material, such as a plastic and/or metal material. In certain embodiments, sampling member 60 comprises a superelastic alloy, for example, a superelastic Ni—Ti alloy. In other embodiments, sampling member 60 comprises a stainless steel alloy. As shown in FIG. 1, sampling member 60 is disposed in the lumen of cannula 40.

As noted above, cannula 40 and/or sampling member 60 may optionally include visualization markers 45 and/or 65 near tips 44 and/or 64 and/or sampling cavity 62 to provide enhanced visualization during insertion and use. For example, when utilizing ultrasonic visualization techniques, visualization markers 45 and/or 65 could comprise an echogenic marker such as a series of small dimple-like indentations on the outer surface of cannula 40 and/or sampling member 60, for example those used on ECHOTIP® Echogenic Needles available from Cook Medical, Bloomington, Ind., USA, to provide enhanced ultrasonic return. In other embodiments, a radiopaque marker, such as a band of bismuth or titanium, could be used to provide enhanced x-ray response during fluoroscopy or other x-ray visualization techniques. Visualization marker 45 and/or 65 may improve the ability of an interventionalist to monitor the position of tips 44 and/or 64 and/or sampling cavity 62 within a patient's body during use.

Figure 4:
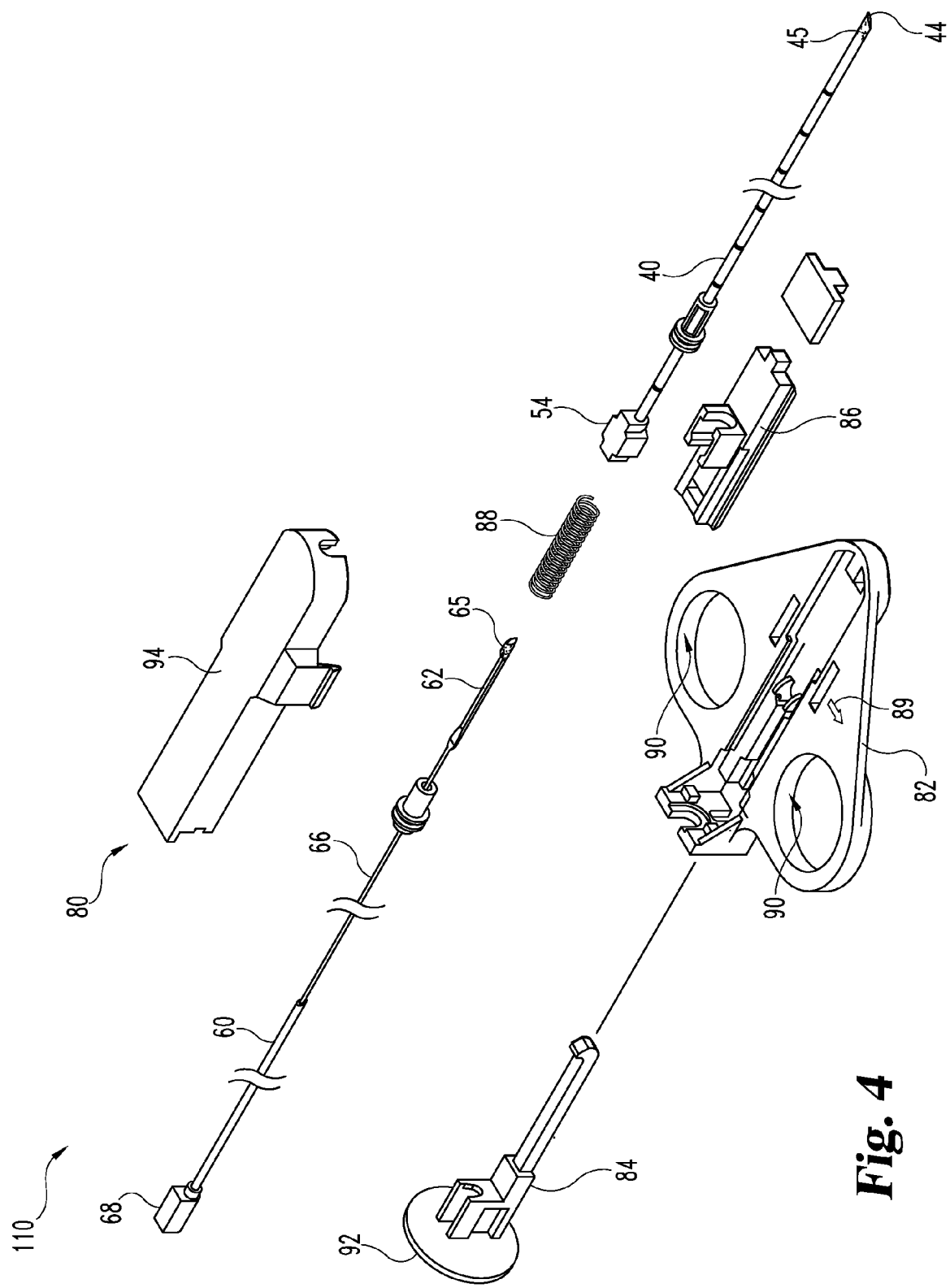
FIG. 4 is an exploded assembly view of the deflectable biopsy device of FIG. 1.
Figure 5:
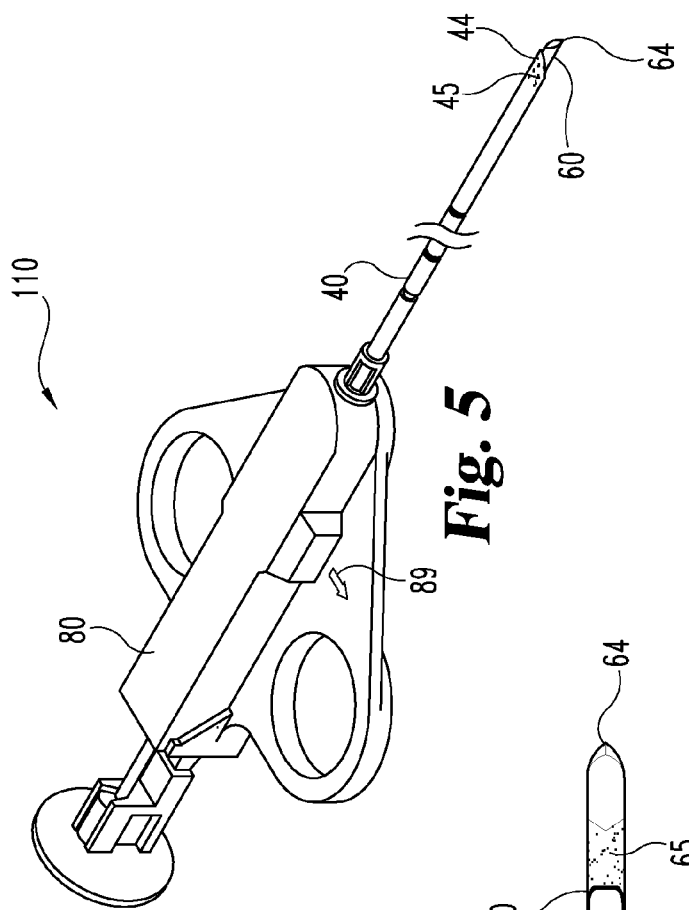
FIG. 5 is a perspective view of the deflectable biopsy device of FIG. 1.

Firing mechanism 80, as illustrated in FIGS. 4 and 5, includes housing 82, actuator 84, drive carriage 86, spring 88, indicator 89 and cover 94. Housing 82 includes finger grips 90 and actuator 84 includes grip 82. Firing mechanism 80 is coupled to cannula hub 54 and wire hub 68 as part of deflectable biopsy device 110. Cannula hub 54 is coupled to drive carriage 86 and wire hub 68 is coupled to actuator 84. When assembled, firing mechanism 80 is "cocked" by pulling grip 92 (and actuator 84) away from housing 82. Actuator 84 interfaces with drive carriage 86 so that when actuator 84 is pulled away from housing 82, drive carriage 86 compresses spring 88 between housing 82 and drive carriage 86. The housing includes a resilient latch that engages the underside of drive carriage 86 in the cocked position. Spring 88 can be subsequently released by pushing grip 92 toward housing 82 generating forward movement of actuator 84 which causes spring 88 to push drive carriage 86 which in turn thrusts cannula 40 over sample cavity 62 of wire 60. Cover 94 fits onto housing 82, covering and protecting spring 88 and sliding engagement between drive carriage 86 and housing 82 from debris and interference. Indicator 89 optionally points in the direction of preformed bend 46. A suitable firing mechanism is disclosed in U.S. Pat. No. 6,056,760 to Koike. (The mention of this firing mechanism is not intended to be limiting or restrictive, it is simply provided as an example of a suitable firing mechanism.)

As described in greater detail below, actuation of firing mechanism 80 propels coring cannula 40 over sampling member 60 to sever and trap tissue within sample cavity 62 of the sampling member 60. The disclosed embodiment of firing mechanism 80 is a single action biopsy device which is effective when used to obtain tissue samples. Alternative embodiments can, for example, utilize double action firing device such as the device disclosed in U.S. Pat. No. 5,538,010 to Darr which may be used in other embodiments in place of the single action device disclosed herein.

Figure 6A:
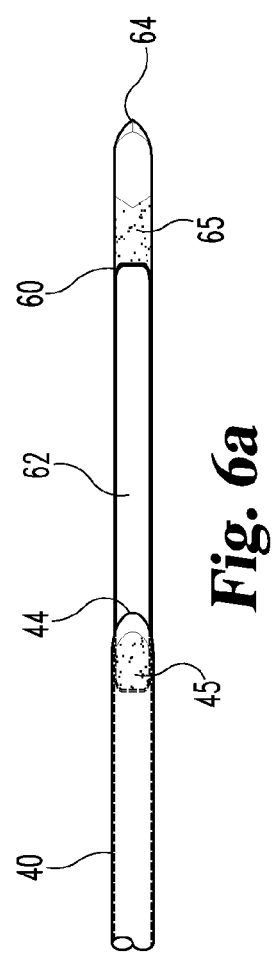
FIG. 6a is a top plan view of distal end of the cannula and wire of FIG. 1 in a cocked position.
Figure 6B:
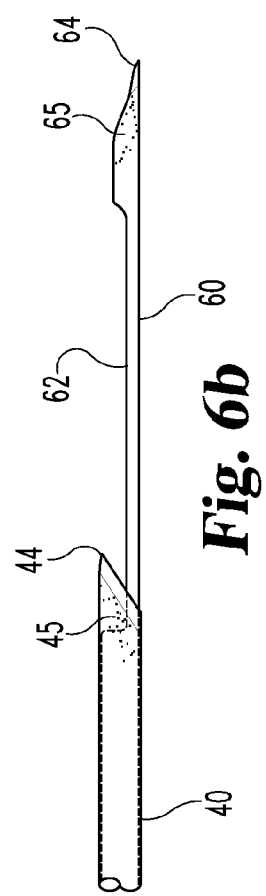

As assembled, deflectable biopsy device 110 includes sampling member 60 disposed in the lumen of cannula 40 with hubs 54 and 68 engaged with firing mechanism 80 as described above. Firing mechanism 80 has two positions (cocked and uncocked) which provide two relative positions between cannula 40 and sampling member 60. In the uncocked position, tip 64 protrudes slightly outside of cannula 40 and tip 44 but with sample cavity 62 substantially covered by cannula 40 with sample cavity 62 substantially lined up with straight wall portion 48. In the cocked position, as illustrated in FIGS. 6a and 6b, cannula 40 and tip 44 are retracted back over sampling member 60, exposing sample cavity 62 outside of cannula 40 and tip 44.

Figure 7:
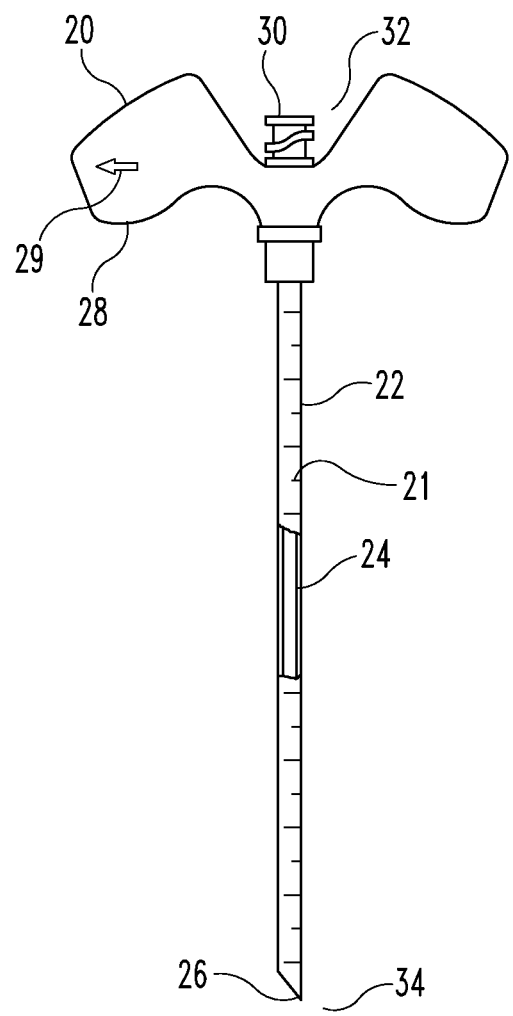
FIG. 7 is an elevational view of an introducer.

FIG. 7 illustrates introducer 20 that is operable to insert and direct deflectable biopsy device into a body. Introducer 20 includes wall 22 defining lumen 24, tip 26 at distal end 34, handle 28 at proximal end 32 and fitting 30. In one mode of construction and operation, during insertion of introducer 20 into the body, deflectable biopsy device 110, in the uncocked position, can be received in introducer 20 with tip 64 of sampling member 60 protruding slightly from tip 26, desirably a needle tip, of introducer 20. This can prevent undesired coring by or occlusion of the introducer 20. Alternatively, while not illustrated, introducer 20 may include a removable trocar received within lumen 24 and connected to fitting 30 during insertion of introducer 20. Such a trocar can block distal end 34 of lumen 24 and prevent undesired coring or occlusion and may further assist in creating access for introducer 20. In some embodiments, the outside of introducer 20 may include depth markers 21 that are directly viewable by a user to determine the depth of insertion through the skin to indicate the approximate depth of insertion. In addition, depth markers 21 can be spaced at regular intervals (such as centimeters) for use as a scale to measure the relative size of internal structures (such as tumors, etc.).

As noted, lumen 24 is arranged and configured to pass cannula 40 therethrough. In this regard, preformed bend 46 of cannula 40 is elastically deformable sufficiently for preformed bend 46 to pass through lumen 24 without substantial plastic deformation. When preformed bend 46 passes into and through lumen 24 it is constrained to conform to the shape of lumen 24. As preformed bend 46 exits lumen 24 through tip 26, preformed bend 46 substantially returns to its unconstrained shape. In the illustrated embodiment, introducer 20 is substantially straight and preformed bend 46 of cannula 40 is constrainable to the substantially straight shape of introducer 20. In alternative embodiments, introducer 20 can be curved. In certain embodiments, introducer 20 or a component attached thereto (e.g. housing 28) can include indicator 29 that remains external to the patient when using introducer 20 and that indicates to the user the open direction of the bevel of tip 26. In some embodiments, it is desired that preformed bend 46 exits through the open portion of tip 26 such that cannula 40 does not impinge against tip 26. (Note: other embodiments of introducer 20 may use other configurations of tip 26 that may or may not have a beveled profile. In yet other embodiments, it may be desirable to alter the relative positioning of the bevel of tip 26 to slightly modify the profile of preformed bend 46 as it exits tip 26.)

FIGS. 8-13 illustrate one embodiment of deflectable biopsy device 110 taking a tissue sample from a sample site within a body. Introducer 20 has been inserted into body 100 through insertion site 108 in skin 102 at a position laterally offset from sample site 104 and obstacle 106. Obstacle 106 broadly encompasses objects or features of body 100 that would be difficult or undesirable to insert introducer 20 through. Obstacle 106 may be between the most direct route between skin 102 and sample site 104. For example, obstacle 106 could include bone, an artery or vein, a duct, a nerve, an organ or obstacle 106 could represent a portion of skin 102 that it would be undesirable to pass introducer 20 into or through.

Figure 8:
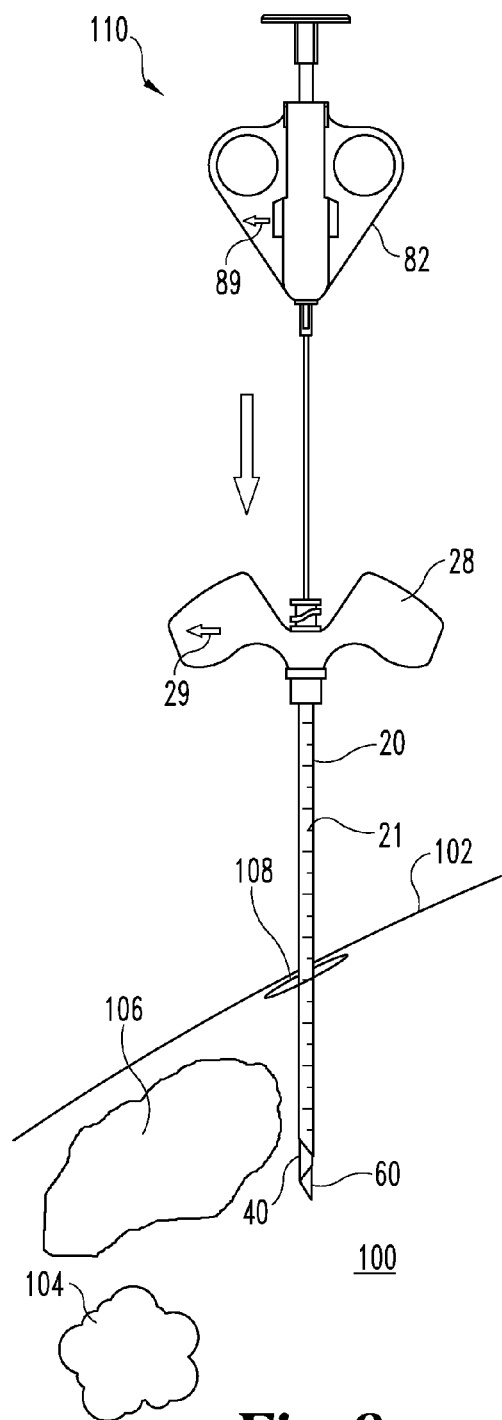
FIG. 8 is an elevational view of an introducer inserted into a body with a deflectable biopsy device partially inserted into the introducer.

In FIG. 8, deflectable biopsy device 110 is partially inserted into introducer 20 with cannula 40 beginning to emerge from introducer 20. The arrow indicates the direction of travel of deflectable biopsy device 110. While not shown, note that, at the point illustrated, the direction that cannula 40 will curve when preformed bend 46 emerges from introducer 20 is controllable by rotating housing 82 (and cannula 40) with respect to handle 28 (and introducer 20). Deflectable biopsy device 110 can be rotated through a full 360° (around the axis of introducer 20). In certain embodiments, cannula 40 or a component attached thereto (e.g. housing 82) can include indicator 89 that remains external of the patient when using device 110 and that indicates to the user the direction in which tip 44 (and preformed bend 46) of the cannula will advance as cannula 40 emerges from distal end 34 of introducer 20. Illustratively, as shown in FIGS. 8-11, this can be accomplished by aligning a recognizable portion of housing 82 with the plane of curvature of bend 46 and, to the extent needed (e.g. as with a symmetrical grip 82 as shown), providing a further marking on the housing 82 (e.g. indicator 89 as the illustrated arrow) to indicate the direction in which the cannula tip 44 will proceed due to the emergence of bend 46 from distal end 34 of introducer 20. When desired, indicator 29 may also be aligned with indicator 89 so that preformed bend 46 exits through the bevel of tip 26.

Figure 9:
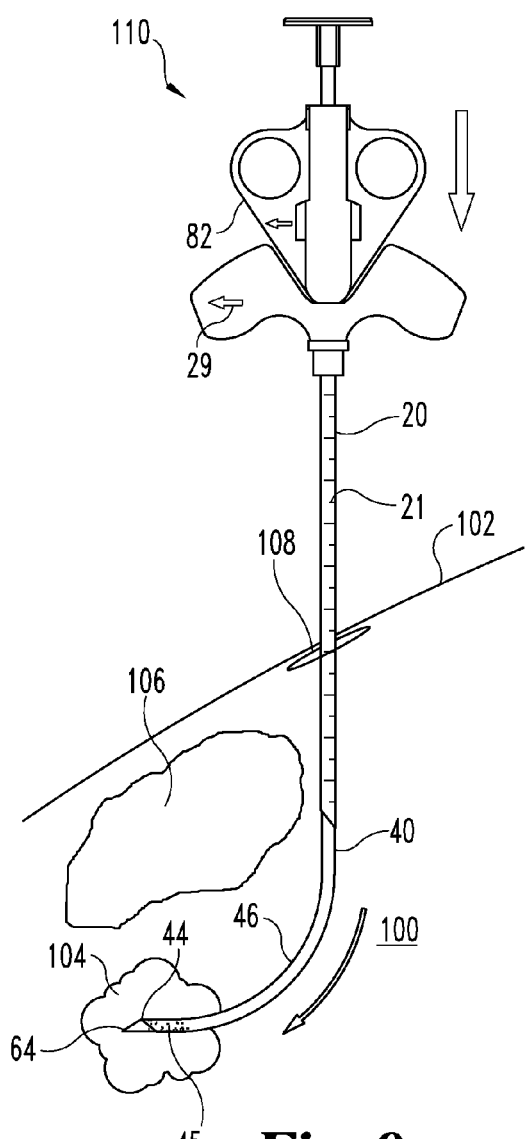
FIG. 9 is an elevational view of the FIG. 8 arrangement with the deflectable biopsy device completely inserted into the introducer with the distal end of the deflectable biopsy device positioned in a sample site.

In FIG. 9, deflectable biopsy device 110 is inserted into introducer 20 with preformed bend 46 fully emerged from introducer 20. Tips 64 and 44 are positioned within sample site 104 and cannula 40 covers sample cavity 62. As preformed bend 46 emerged from introducer 20 it returned to its unconstrained bent shape so that tip 64 substantially passed through the space filled by cannula 40. Therefore, in the FIG. 9 configuration, cannula 40 (and preformed bend 46) are in a substantially unstressed state.

Figures 10, 11:
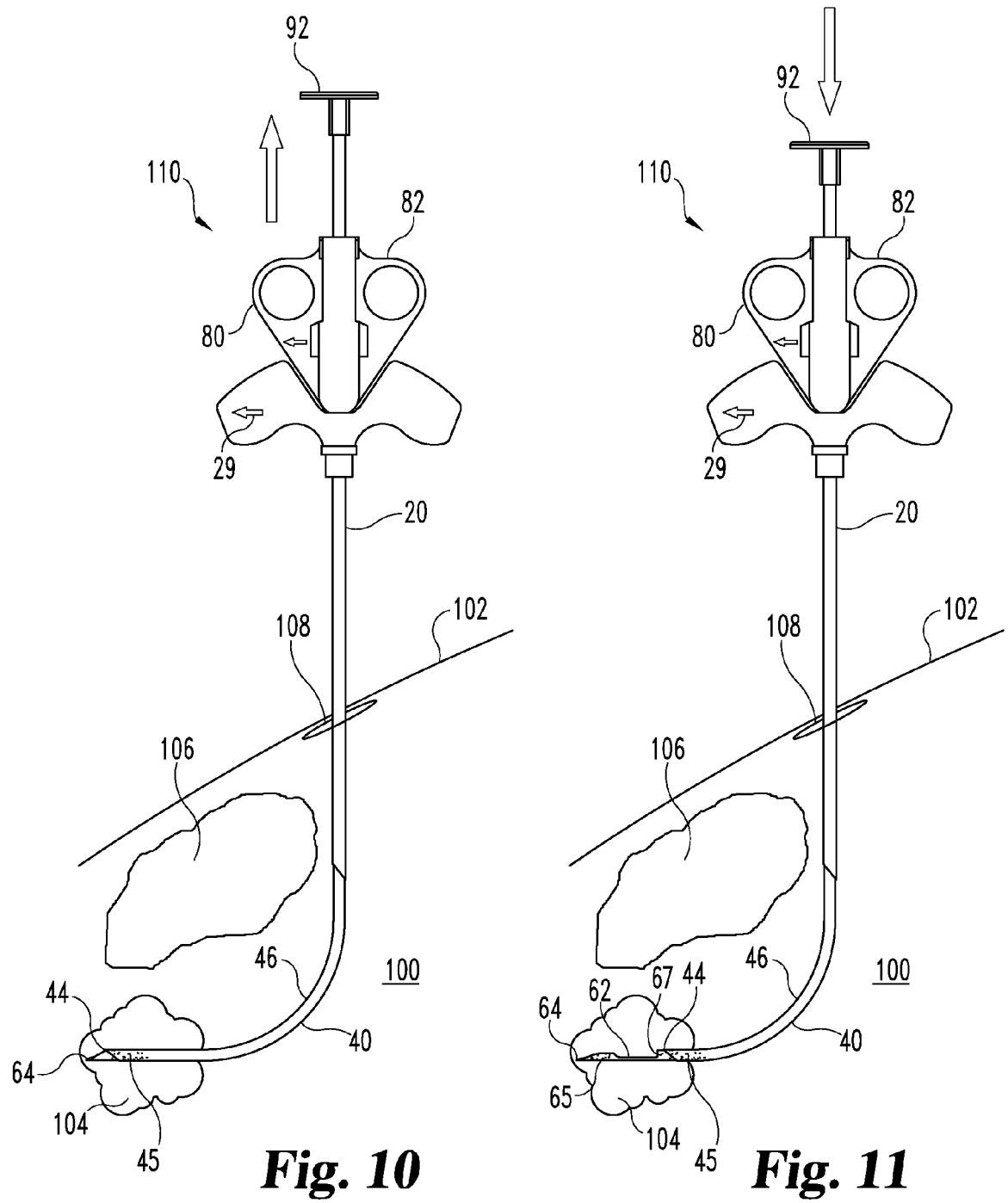
FIG. 10 is an elevational view of the FIG. 9 arrangement in a cocked configuration.
FIG. 11 is an elevational view of the FIG. 9 arrangement in an initial triggered configuration.

In FIG. 10, firing mechanism 80 is in the cocked position with grip 92 pulled away from housing 82 simultaneously compressing spring 88. Cannula 40 and wire 60 substantially remain substantially fixed in relationship to each other when firing mechanism 80 is cocked In FIG. 11, grip 92 has been partially depressed toward housing 82 thereby pushing wire 60 out of cannula 40 thereby exposing sample cavity 62 inside sample site 104 with tip 44 perched on shoulder 67. As sample cavity 62 is exposed inside sample site 104, a portion of the tissue from sample site 104 moves into sample cavity 62 due to interstitial pressure.

Figure 12:
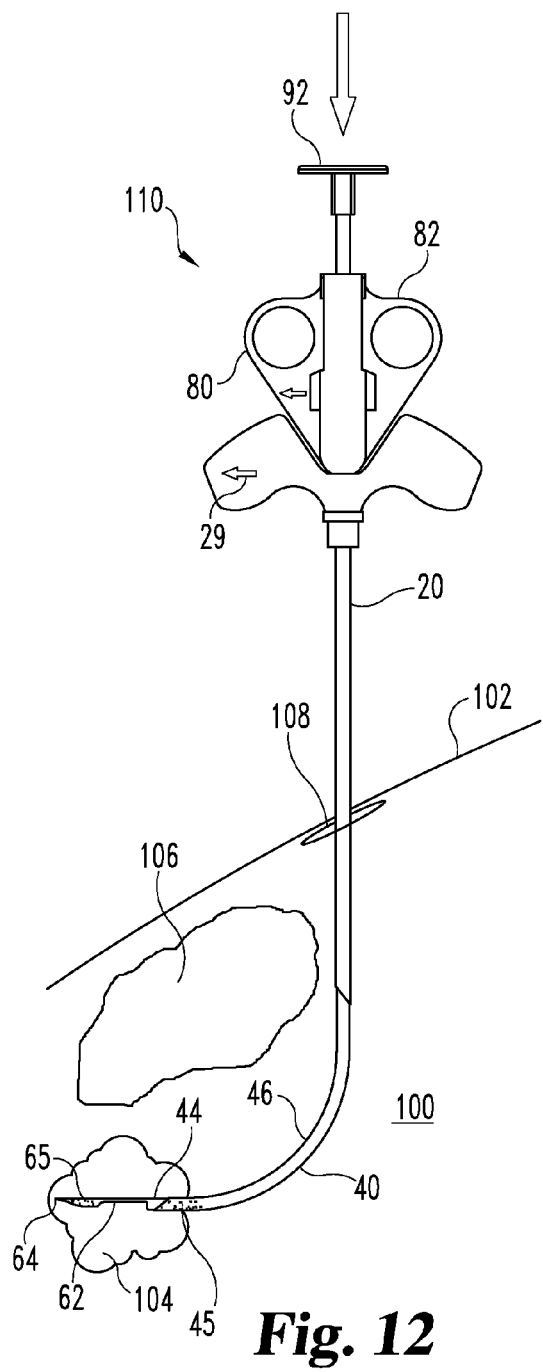
FIG. 12 is an elevational view of an alternative embodiment of the FIG. 11 configuration.

Referring to FIG. 12, an alternative configuration of wire 60 and cannula 40 is illustrated with sampling cavity 62 rotated approximately 180° as compared to the configuration illustrated in FIG. 11. In other embodiments, sampling cavity 62 can be oriented in any desired direction.

Figure 13:
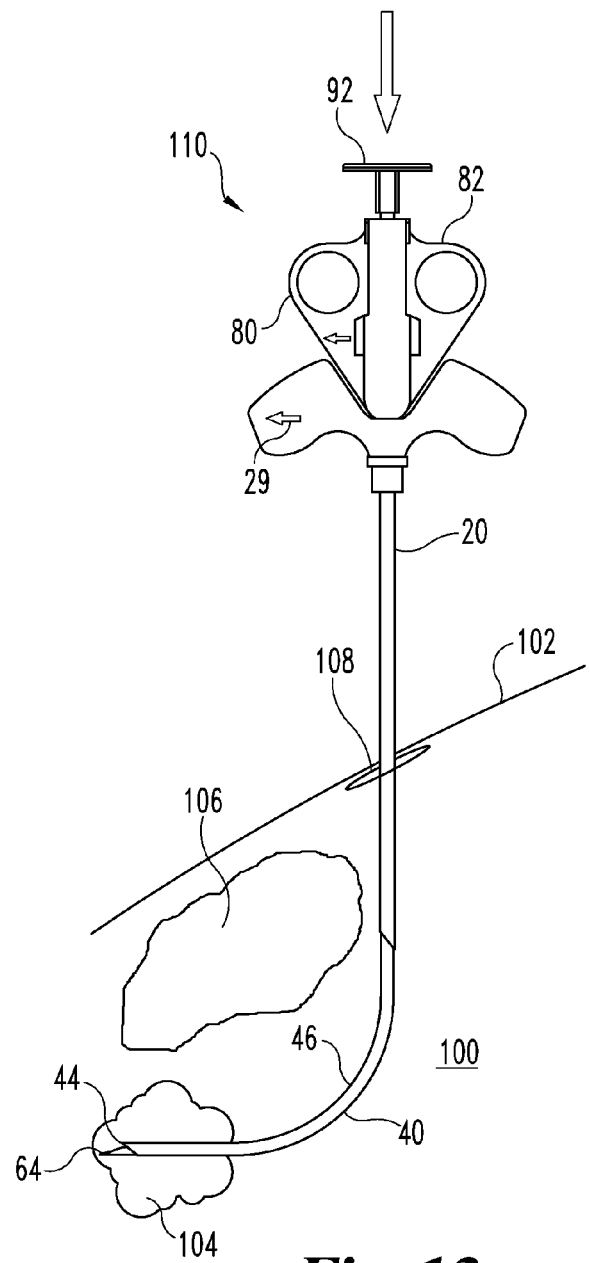
FIG. 13 is an elevational view of the FIGS. 9, 10 and 11 arrangement in a final fired configuration.

In FIG. 13, grip 92 has been completely depressed toward housing 82 thereby releasing the spring in firing mechanism 80 causing cannula 40 to cover sample cavity 62. This generates a cutting action in which tip 44 cuts through and severs a portion of tissue from sample site 104 that moved into sample cavity 62 prior to the firing of firing mechanism 80. In certain embodiments, during the cutting action that occurs between sampling member 60 and cannula 40, sampling member 60 remains constrained by cannula 40 to a condition bent from its relaxed (unconstrained) configuration while preformed bend 46 of cannula 40 remains in its relaxed (unconstrained) configuration. That portion of sample site 104 is then retained inside sample cavity 62 and cannula 40 and can be recovered for further investigation and testing by removing deflectable biopsy device 110 from introducer 20 and cocking firing mechanism 80 to once again retract cannula 40 over sampling member 60 to expose sample cavity 62.

Figure 14A:
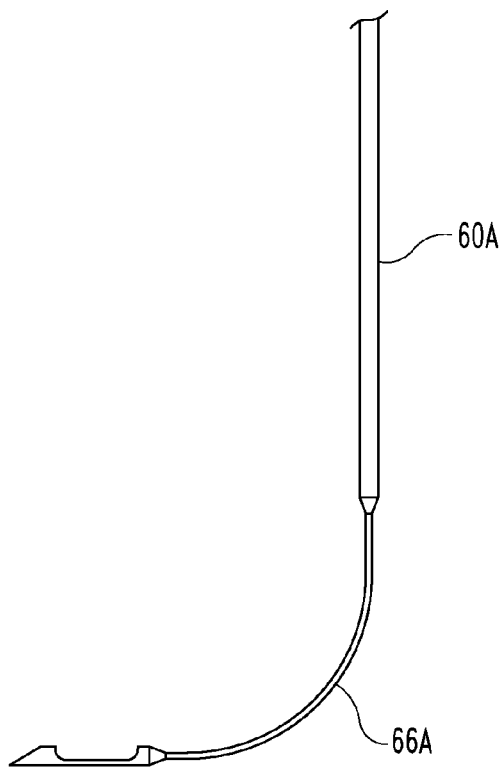
FIG. 14a is a partial elevational view of an alternative embodiment of a wire.
Figure 14B:
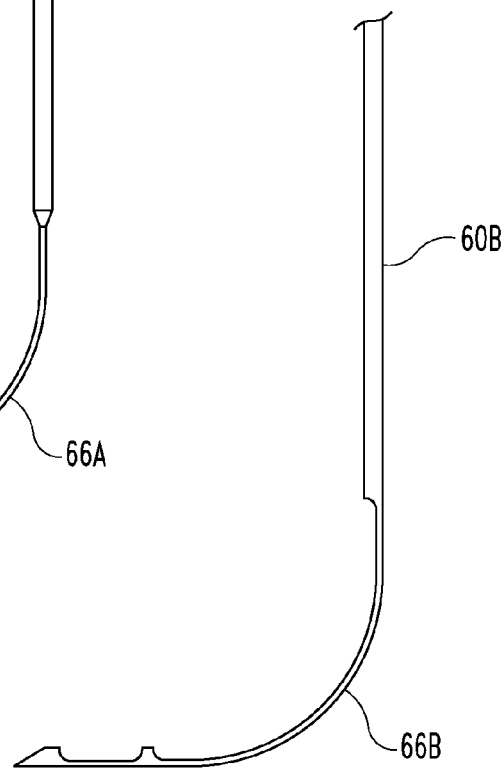
FIG. 14b is a partial elevational view of an alternative embodiment of a wire.
Figure 14C:
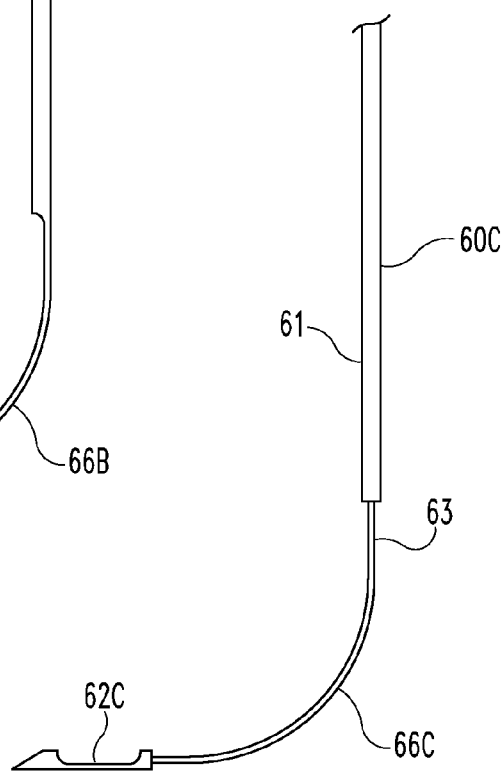
FIG. 14c is a partial elevational view of an alternative embodiment of a wire.

FIGS. 14*a*-14*c* illustrate alternative embodiments of sampling member 60. In FIG. 14*a*, wire 60A is formed by centerless grinding to create a more flexible portion 66A from one continuous wire (that also includes a tip and sample cavity formed from or attached to the wire). In FIG. 14*b*, wire 60B is formed by grinding flexible portion 66B on one side of one continuous wire, cannula or other suitable elongate member (that also includes a tip and sample cavity formed therein or attached thereto). In FIG. 14*c*, wire 60C is assembled from separate large gauge wire 61, small gauge wire 63 and sample cavity 62*c*. Assembly can be by soldering, welding or otherwise permanently attaching the components together with flexible portion 66C generally corresponding with small gauge wire 63. Illustrative elongate materials that can be used to create sampling member 60 include wire and/or cannula as noted above as well as cable-tube, multi-filar cable, or any combination of these or potentially other materials.

In various embodiments of sampling member 60, flexible portion 66 provides substantially no resistance to bending and member 60 can be rotated with respect to cannula 40 to vary the angle at which sampling cavity 62 is presented when cannula 40 is retracted. However, in alternative embodiments of sampling member 60, including where member 60 comprises a superelastic alloy, flexible portion 66 can provide substantial resistance to bending. In such embodiments, the bending characteristics of member 60 can be used to alter the bending characteristics of cannula 40 (and thereby deflectable biopsy device 110). For example, if member 60 includes a preformed bend in flexible portion 66 that is oriented corresponding to preformed bend 46, then sampling member 60 can assist cannula 40 in returning to its unstressed curved state after exiting lumen 20. Alternatively, bending characteristics of cannula 40 could be varied by rotating sampling member 60, having a preformed bend, with respect to cannula 40. This could vary the effective angle of preformed bend 46. In yet another embodiment, sampling member 60 can comprise a superelastic alloy without a preformed bend (providing a generally straight member 60 when unconstrained) such that member 60 is in a stressed condition when located within preformed bend 46 of cannula 40 outside of introducer 20.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected.

I claim:

1. A deflectable biopsy device for collecting a tissue biopsy, comprising: a cannula comprising a wall between a proximal end and a distal end defining a cannula lumen therebetween, the cannula, when in an unstressed condition defines a geometry including a preformed bend having a first shape positioned between the proximal and distal ends, wherein said preformed bend is constrainable by a constraining force to alter the geometry of said preformed bend to a second shape and wherein, upon release of the constraining force, the geometry of said preformed bend substantially returns to the first shape; a sampling member slidably disposed within said cannula lumen, said sampling member defining a sampling cavity and being cooperable with said cannula to sever and trap a tissue biopsy in said sampling cavity, wherein said sampling member and said cannula are constructed and arranged to allow the sampling member to slidably navigate the first shape of the preformed bend of said cannula without binding, and wherein said sampling member includes a first portion and a second portion, wherein said second portion is positioned between said first portion and said sampling cavity, and wherein said second portion is more flexible than said first portion; and a firing mechanism engaged to a cannula hub at the proximal end of said cannula and a sampling member hub at a proximal end of said sampling member, wherein said firing mechanism is constructed and arranged to rapidly move said cannula relative to said sampling member from a second position in which said sampling member extends through said cannula with the sampling cavity protruding outside of and not covered by said cannula to a first position in which the sampling cavity is covered by said cannula, and wherein, in the first position, said second portion of said sampling member is aligned with said preformed bend of said cannula.

2. The deflectable biopsy device of claim 1, further comprising an introducer comprising an introducer lumen sized to receive said cannula through said introducer lumen, wherein said introducer lumen is constructed and arranged to constrain said preformed bend to alter the shape of said preformed bend to substantially conform to the shape of said introducer lumen when said preformed bend is inserted into said introducer lumen, wherein the geometry of said preformed bend is the first shape when said cannula is not received in said introducer.

3. The deflectable biopsy device of claim 2, wherein said cannula is freely rotatable in said introducer.

4. The deflectable biopsy device of claim 2, wherein said cannula is slidably deployable from the distal end of said introducer whereby, at exiting from the distal end of said introducer, the geometry of said preformed bend substantially returns to the first shape and wherein said cannula exits said introducer at a different angular orientation than the angular orientation of the distal end of said introducer.

5. The deflectable biopsy device of claim 1, wherein said cannula further comprises a tip on the distal end constructed and arranged to cut tissue.

6. The deflectable biopsy device of claim 1, wherein said sampling member further comprises a tip on the distal end constructed and arranged to penetrate tissue.

7. The deflectable biopsy device of claim 1, wherein said cannula comprises a superelastic material.

8. The deflectable biopsy device of claim 1, wherein said cannula lumen is defined by an uninterrupted and continuous wall between the distal and proximal ends of said cannula.

9. The deflectable biopsy device of claim 1, wherein said cannula further comprises a substantially straight walled portion extending between the distal end and said preformed bend, wherein, in the first position, said sampling cavity lines up with said substantially straight wall portion of said cannula.

10. The deflectable biopsy device of claim 1, wherein said preformed bend is angled between 40 and 90 degrees.

11. The deflectable biopsy device of claim 1, wherein said preformed bend is angled approximately 90 degrees.

12. The deflectable biopsy device of claim 1, wherein the constrained configuration is substantially straight.

13. The deflectable biopsy device of claim 1, wherein said sampling member is freely rotatable in said cannula.

14. The deflectable biopsy device of claim 1, wherein said second portion is constructed and arranged to not alter the shape of said preformed bend in said first position.

15. The deflectable biopsy device of claim 1, wherein said second portion has a smaller cross-sectional area than said first portion.

16. A deflectable biopsy device for collecting a tissue biopsy, comprising:
    a cannula defining a cannula lumen, the cannula, when in an unstressed condition, defines a geometry including a preformed bend, wherein said cannula comprises a superelastic material;
    an introducer defining an introducer lumen sized to receive said cannula through said introducer lumen;
    a sampling member disposed within the cannula lumen, said sampling member comprising a sampling cavity, a first portion and a second portion positioned between said first portion and said sampling cavity, wherein said second portion has a smaller cross-sectional area than said first portion, wherein said second portion is aligned with said preformed bend; and
    wherein the cannula and sampling member are movable relative to one another so as to sever and collect a tissue biopsy in the sampling cavity, wherein said cannula is movable relative to said introducer through said introducer lumen and wherein, when said cannula passes through said introducer, said cannula exits said introducer at a different angular orientation than the angular orientation of the distal end of said introducer, and wherein said sampling member is constructed and arranged to slidably navigate the preformed bend of said cannula without binding.

17. The deflectable biopsy device of claim 16, wherein said wall is continuous whereby said cannula lumen is uninterrupted between the distal and proximal ends.

18. The deflectable biopsy device of claim 16, wherein said sampling member is freely rotatable in said cannula.

19. A deflectable biopsy device for collecting a tissue biopsy, the deflectable biopsy device comprising:
    a cannula comprising a wall between a proximal end and a distal end defining a cannula lumen therebetween, the cannula, when in an unstressed condition defines a geometry including a preformed bend having a first shape positioned between the proximal and distal ends and a straight wall portion extending between the preformed bend and the distal end, wherein said preformed bend is constrainable by a constraining force to alter the geometry of said preformed bend to a second shape and wherein, upon release of the constraining force, the geometry of said preformed bend substantially returns to the first shape, wherein said cannula lumen defines an uninterrupted and continuous wall between the distal and proximal ends of said cannula;

a sampling member slidably disposed within said cannula lumen, said sampling member defining a sampling cavity and being cooperable with said cannula to sever and trap a tissue biopsy in said sampling cavity, said sampling member including a first portion and second portion positioned between said first portion and said sampling cavity, wherein said sampling member is constructed and arranged to slidably navigate the preformed bend of said cannula without binding, and wherein said second portion of said sampling member navigates the preformed bend and is more flexible than said first portion of said sampling member; and a firing mechanism engaged to a cannula hub at the proximal end of said cannula and a sampling member hub at a proximal end of said sampling member, wherein said firing mechanism is constructed and arranged to rapidly move said cannula relative to said sampling member from a second position in which said sampling member extends through said cannula with the sampling cavity protruding outside of and not covered by said cannula to a first position in which the sampling cavity is covered by said cannula, wherein, in the first position, the sampling cavity lines up with said straight wall portion of said cannula.

20. The deflectable biopsy device of claim 19, further comprising an introducer comprising an introducer lumen sized to receive said cannula through said introducer lumen, wherein said introducer lumen is constructed and arranged to constrain said preformed bend to alter the shape of said preformed bend to substantially conform to the shape of said introducer lumen when said preformed bend is inserted into said introducer lumen, wherein the geometry of said preformed bend is the first shape when said cannula is not received in said introducer.

21. The deflectable biopsy device of claim 19, wherein said sampling member further comprises a shoulder located between said second portion and the sampling cavity, wherein said second portion has a smaller cross section than said shoulder and wherein, in the second position, the distal end of said cannula is perched on said shoulder.

\* \* \* \* \*